(12) United States Patent
Safai (10) Patent No.: US 10,502,695 B2
(45) Date of Patent: Dec. 10, 2019

(54) AUTOMATED INSPECTION OF FOREIGN MATERIALS, CRACKS AND OTHER SURFACE ANOMALIES

(71) Applicant: The Boeing Company, Chicago, IL (US)

(72) Inventor: Morteza Safai, Seattle, WA (US)

(73) Assignee: THE BOEING COMPANY, Chicago, IL (US)

(*) Notice: Subject to any disclaimer, the term of this patent is extended or adjusted under 35 U.S.C. 154(b) by 58 days.

(21) Appl. No.: 15/678,670

(22) Filed: Aug. 16, 2017

(65) Prior Publication Data

US 2019/0056334 A1    Feb. 21, 2019

(51) Int. Cl.
| | | |
|---|---|---|
| *B32B 41/00* | (2006.01) | |
| *G01N 21/956* | (2006.01) | |
| *G06T 7/00* | (2017.01) | |
| *G06K 9/62* | (2006.01) | |
| *H04N 5/247* | (2006.01) | |
| *H04N 5/225* | (2006.01) | |
| *B32B 37/14* | (2006.01) | |
| *G01N 21/94* | (2006.01) | |

(52) U.S. Cl.
CPC .......... *G01N 21/956* (2013.01); *B32B 37/14* (2013.01); *G01N 21/94* (2013.01); *G06K 9/6202* (2013.01); *G06T 7/001* (2013.01); *H04N 5/2256* (2013.01); *H04N 5/247* (2013.01); *B32B 2605/18* (2013.01); *G01N 2201/0628* (2013.01);
(Continued)

(58) Field of Classification Search
CPC ............... G01N 21/956; G01N 21/94; G01N 2201/0628; B32B 37/14; B32B 2605/18; G06T 7/001; G06T 2207/30164; G06T 2207/10024; G06T 2207/10152; G06K 9/6202; H04N 5/247; H04N 5/2256
USPC ........................ 156/64, 350, 351, 378, 379
See application file for complete search history.

(56) References Cited

U.S. PATENT DOCUMENTS

| | | |
|---|---|---|
| 5,365,084 A | 11/1994 | Cochran et al. |
| 2005/0225753 A1 | 10/2005 | Engelbart et al. |

(Continued)

FOREIGN PATENT DOCUMENTS

| | | |
|---|---|---|
| DE | 10 2015 008409 A1 | 1/2017 |
| DE | 10 2015 217173 A1 | 3/2017 |

OTHER PUBLICATIONS

Chatterjee, "Advanced Color Machine Vision and Applications," Graftek Imaging, Inc., Mar. 26, 2014, 161 pages.
(Continued)

*Primary Examiner* — Michael N Orlando
*Assistant Examiner* — Joshel Rivera
(74) *Attorney, Agent, or Firm* — MH2 Technology Law Group LLP (57) ABSTRACT

An inspection system for detecting defects in a workpiece can include an illumination source for illuminating a first section of the workpiece with a patterned light, wherein the illumination source does not illuminate a second section of the workpiece. The inspection system further includes a feedback camera for imaging the first section and producing a first output, and a background camera for imaging the second section and producing a second output. A processor compares the first output with the second output, and a controller alters the patterned light that is output by the illumination source based on the comparison. This feedback control continues until the background is suitably homogeneous or camouflaged compared to the defect, such that the visibility and/or detectability of the defect is increased.

20 Claims, 5 Drawing Sheets

(52) U.S. Cl.
    CPC ............... *G06T 2207/10024* (2013.01); *G06T 2207/10152* (2013.01); *G06T 2207/30164* (2013.01)

(56) References Cited

U.S. PATENT DOCUMENTS

| | | |
|---|---|---|
| 2006/0114463 A1* | 6/2006 | Detinkin ................ G01N 21/49 356/431 |
| 2011/0141725 A1* | 6/2011 | Brusilovsky ............ F21S 6/003 362/231 |
| 2011/0299720 A1 | 12/2011 | Nolen et al. |
| 2016/0221048 A1* | 8/2016 | Safai ........................ B08B 5/02 |
| 2016/0266048 A1 | 9/2016 | Liang et al. |
| 2016/0366744 A1 | 12/2016 | Clout et al. |

OTHER PUBLICATIONS

Author Unknown, "Color Thresholding Algorithm for Vision-Based Inspection Applications," http://www.ni.com/white-paper/3097/en/, Aug. 25, 2016, 4 pages.
Keirouz, "Opening New Doors With Color Machine Vision," https://www.qualitydigest.com/oct98/html/color.html, 1998, 7 pages.
Shabayek et al., "Visual Behaviour Based Bio-Inspired Polarization Techniques in Computer Vision and Robotics," HAL Archives, https://hal.archives-ouvertes.fr/hal-00760950, Dec. 2012, 31 pages.
Extended European Search Report dated Feb. 1, 2019 in corresponding European Patent Application No. 18183915.0.

* cited by examiner

AUTOMATED INSPECTION OF FOREIGN MATERIALS, CRACKS AND OTHER SURFACE ANOMALIES

FIELD

The present teachings relate to the field of manufacturing inspection and, more particularly, to inspection systems including surface illumination and imaging subsystems.

BACKGROUND

Manufacturing components for vehicles such as aircraft and aerospace vehicles, ground vehicles, etc., from fiber sheets is well known. A composite part including a plurality of composite plies or sheets that are pre-impregnated with an uncured resin (i.e., prepregs) may be assembled during a layup process. During layup, several (e.g., 20, 40, or more) uncured composite plies are stacked, and then air that may be trapped between each of the several plies may be removed using a vacuum during a "debulk" process. Subsequently, the resin may be cured in an oven or an autoclave.

The fiber sheets should remain free from defects such as contaminating particulates of foreign material (e.g., bagging materials, tape, braiding material, etc.) and cracks, pits, and other defects during the layup process. These defects can result in delamination, porosity, and wrinkling of the component if they remain subsequent to curing which can, in turn, result in scrapping of the component.

SUMMARY

The following presents a simplified summary in order to provide a basic understanding of some aspects of one or more implementations of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

A method for inspecting a workpiece according to an implementation of the present teachings includes outputting a patterned light onto a first section of the workpiece using an illumination source, wherein the first section of the workpiece reflects the patterned light, imaging the patterned light reflected from the first section of the workpiece using a feedback camera to generate a first output, and imaging a second section of the workpiece that is not illuminated by the illumination source using a background camera to generate a second output. The method further includes comparing the first output to the second output, and altering the patterned light output by the illumination source by changing one or more of an intensity, a hue, a saturation, and a color of the patterned light based on the comparing of the first output to the second output, thereby increasing a contrast of one or more defects located in the first section of the workpiece.

The illumination source can include at least one million organic light emitting diodes (OLEDs), and the altering of the patterned light output by the illumination source can include individually controlling the intensity of each of the OLEDs, and each OLED may be configured to output at least 1000 lux. The method can further include displaying data obtained from the first output from the feedback camera onto a display for inspection by an operator, and can also include imaging the patterned light reflected from the first section of the workpiece using an inspection camera to generate a third output, sending data obtained from the third output from the inspection camera to a processor, and using the processor to analyze the data obtained from the third output to detect the one or more defects in the first section of the workpiece. In an implementation, the method can further include detecting the one or more defects on or within the workpiece during the comparing, using a controller to position a pressure conveying system relative to the one or more defects, and activating the pressure conveying system to dislodge the one or more defects from the workpiece. The activating of the pressure conveying system can include at least one of activating a blower to output a stream of air to dislodge the one or more defects and activating a vacuum to apply a vacuum force to the one or more defects.

The altering of the patterned light can result in homogenizing the light reflected from the second section of the workpiece, except for light reflected from the one or more defects. The method can further include depositing a first composite layer of the workpiece onto a working surface using a composite layup system, wherein the first section of the workpiece is a first section of an aircraft subassembly and the second section of the workpiece is a second section of the workpiece, performing the imaging of the patterned light reflected from the first section of the aircraft subassembly, depositing a second composite layer of the aircraft subassembly onto the first composite layer, outputting the patterned light onto a first section of the second composite layer using the illumination source, wherein the first section of the second composite layer reflects the patterned light, and imaging the patterned light reflected from the first section of the second composite layer using the feedback camera to generate a third output.

In another implementation according to the present teachings, an inspection system can include an illumination source configured to output a patterned light and to illuminate a first section of a workpiece with the patterned light, a feedback camera configured to image the patterned light from the illumination source that is reflected from the first section of the workpiece, and to generate a first output, a background camera configured to image a second section of the workpiece that is not illuminated by the illumination source, and to generate a second output, and a controller coupled to the illumination source, the feedback camera, and the background camera, wherein the controller is configured to alter the patterned light output by the illumination source by changing one or more of an intensity, a hue, a saturation, and a color of the patterned light based on a comparison of the first output to the second output, thereby increasing a contrast of one or more defects located in the first section of the workpiece. The illumination source can be an organic light emitting diode (OLED) display comprising at least one million OLEDs. The controller can be configured to alter the patterned light output by the illumination source by individually controlling each OLED of the plurality each OLEDs with respect to light intensity. Each OLED can be configured to output an intensity of at least 1000 lux and to have a luminous efficiency of at least 100 lumens per Watt.

The inspection system can further include a visual display for displaying data obtained from the first output generated by the feedback camera, and the visual display can be configured to display an image of the one or more defects located in the first section of the workpiece imaged by the feedback camera for review by an operator. The inspection system can further include an inspection camera for imaging the second portion of the workpiece during the illumination by the illumination source and to provide a third output to the controller.

In an implementation, the inspection system can include a pressure conveying system electrically coupled to, and controlled by, the controller, wherein the controller is configured to position the pressure conveying system relative to the one or more defects detected during the comparison using the third output from inspection camera, and to activate the pressure conveying system to dislodge the one or more defects from a surface of the workpiece. The pressure conveying system can include at least one of a blower configured to output a stream of air to dislodge the one or more defects and a vacuum configured to apply a vacuum force to the one or more defects. The illumination source can include an array of at least one million illumination elements that are individually controllable with respect to intensity, and the controller is configured to vary the intensity, hue, saturation, color, and pattern of the light output by the illumination source such that the feedback camera images a surface that is homogenous with respect to intensity, hue, saturation, and color, except for the one or more defects on or within the surface of the workpiece.

In another implementation, an aircraft manufacturing line can include a composite layup system configured to deposit a plurality of layers of a composite aircraft subassembly onto a working surface and an inspection system for inspecting the composite aircraft subassembly during a deposition of the plurality of layers. The inspection system can include an illumination source configured to output a patterned light and to illuminate a first section of a workpiece with the patterned light, a feedback camera configured to image the patterned light from the illumination source that is reflected from the first section of the workpiece, and to generate a first output, a background camera configured to image a second section of the workpiece that is not illuminated by the illumination source, and to generate a second output, and a controller coupled to the illumination source, the feedback camera, and the background camera, wherein the controller is configured to alter the patterned light output by the illumination source by changing one or more of an intensity, a hue, a saturation, and a color of the patterned light based on a comparison of the first output to the second output, thereby increasing a contrast of one or more defects located in the first section of the workpiece.

BRIEF DESCRIPTION OF THE DRAWINGS

The accompanying drawings, which are incorporated in, and constitute a part of this specification, illustrate implementations of the present teachings and, together with the description, serve to explain the principles of the disclosure. In the figures.

It should be noted that some details of the figures have been simplified and are drawn to facilitate understanding of the present teachings rather than to maintain strict structural accuracy, detail, and scale.

DETAILED DESCRIPTION

Reference will now be made in detail to exemplary implementations of the present teachings, examples of which are illustrated in the accompanying drawings. Generally, the same reference numbers will be used throughout the drawings to refer to the same or like parts.

Eliminating defects during manufacture of a large component such as a composite aircraft subassembly from a plurality of composite plies is important to reduce costs. However, foreign materials and other defects can be difficult to detect, for example, because the surface color of composite or metallic structures may camouflage or mask the foreign material, which may be the same color and material as the composite ply itself. Once the composite structure has been cured in autoclave or by vacuum bag, these foreign materials can result in rejection of a large and expensive structure during subsequent visual inspection or nondestructive testing. Currently, there are no inspection techniques that can detect both cracks and contamination in a finished part, and thus detection of cracks and contamination during the manufacturing process is critical.

An implementation of the present teachings can include an inspection system and method for detecting defects during the manufacture of a composite part and other articles of manufacture. The inspection system is discussed herein with reference to a manufacturing line including a layup process that forms a structure such as a laminated aircraft component, although it will be appreciated that the inspection may be employed for other uses. During the formation of an aircraft component, up to 40 or more carbon composite plies that are pre-impregnated with an adhesive resin may be stacked and processed.

Figure 1:
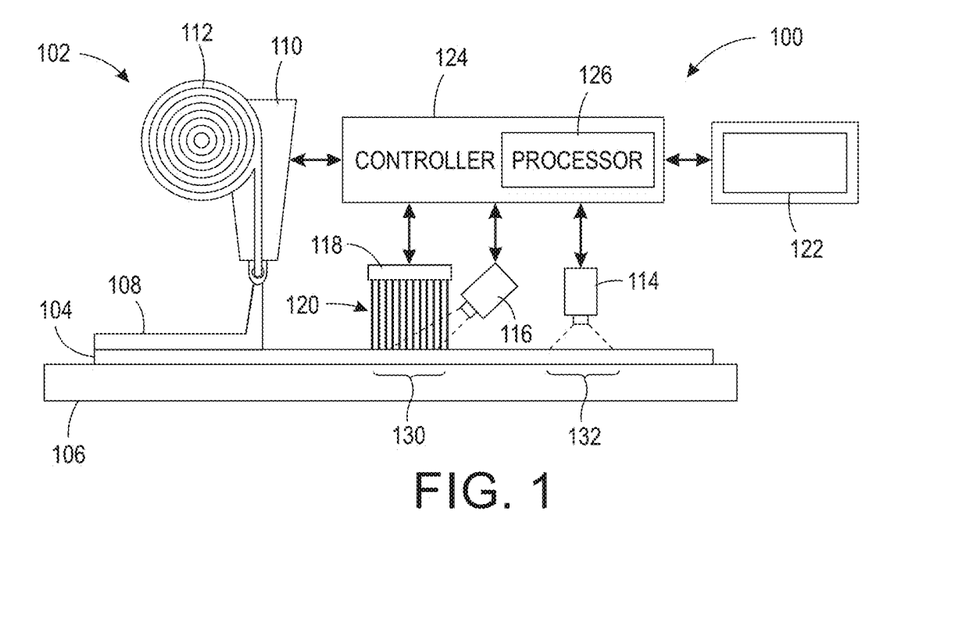
FIG. 1 is a schematic depiction of an inspection system according to an implementation of the present teachings.

FIG. 1 is a schematic illustration depicting an inspection system 100 in accordance with an implementation of the present teachings during use for inspecting of a workpiece such as a composite laminate during a layup process. The layup process uses a composite layup system 102 that can be used to place one or more layers, such as at least a first composite ply 104 onto a base 106, for example a work surface such as a layup table, and a second composite ply 108 on the first composite ply 104. It will be appreciated that the base 106 may be or include one or more underlying structures such as one or more other composite plies upon which the first composite ply 104 is positioned. A layup head 110 and a composite ply supply 112 can move across the base 106 during placement of the first composite ply 104 and the second composite ply 108 at a speed of up to 3000 inches per minute, which can be considered a relatively high rate of speed for manufacturing. Formation of components using a layup system 102 is well known in the art.

During the layup process, stray composite fibers, bagging materials, braiding materials, tape, and other foreign materials can become detached and positioned between the composite plies 104, 108. If these foreign materials are not detected and remain, they can cause wrinkling, porosity, and/or delamination of the completed structure which, in turn, can result in rework or scrapping of the completed structure. These foreign materials, as well as cracks that may develop, are difficult to detect, for example, because of the surface color of the composite plies or metallic structures may camouflage or mask the foreign material. Once the composite structure has been cured in autoclave or by vacuum bag, these foreign materials can result in rejection of a large structure during subsequent visual inspection or non-destructive testing.

The inspection system 100 of FIG. 1 includes a background camera 114, a feedback camera 116, an illumination source 118 configured to output a patterned light 120 (i.e., a pattern of light, light output, patterned light output), and a display 122, each electrically coupled with a controller 124. The inspection system 100 can further include a processor 126 such as one or more microprocessors or a processing system, which may be part of the controller 124 as depicted or may be a separate system component electrically coupled to the controller 124.

Figure 2:
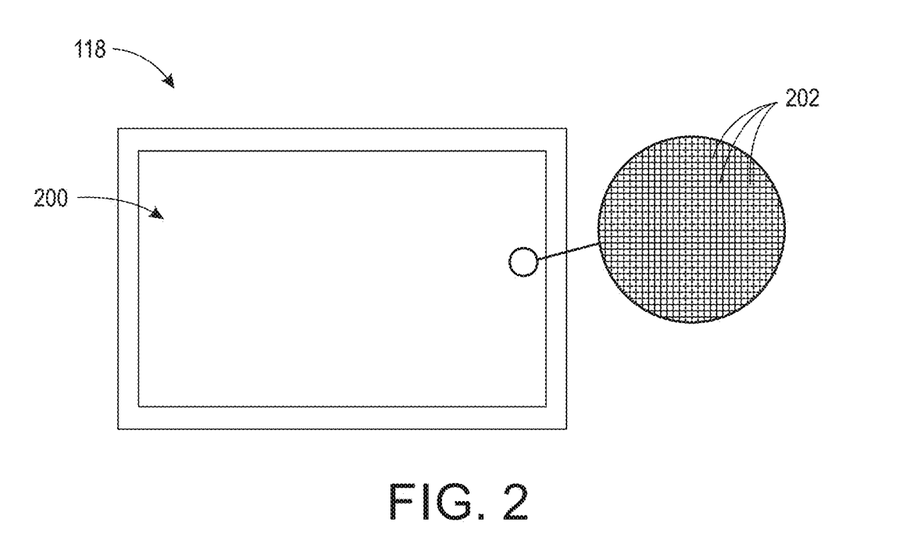
FIG. 2 is a plan view with a magnified cutaway of an organic light emitting diode display according to an implementation of the present teachings.

The illumination source 118 is configured to output the patterned light 120 onto a first section 130 of one of the composite plies, for example, the first composite ply 104 as depicted in FIG. 1. The illumination source 118 can be or include an organic light emitting diode (OLED) array 200 (FIG. 2) including a plurality of OLEDs 202 (depicted in the magnified cutaway detail of FIG. 2), or another illumination source configurable as described herein. Each OLED of the plurality of OLEDs 202 can be configured to output an intensity of at least 1000 lux, and can have a luminous efficiency of at least 100 lumens per Watt (lm/W), or at least 125 lm/W, or at least 150 lm/W, to enable a very bright illumination of the background, which helps to be able to discern different colors. The illumination source 118 is electrically coupled to, and can be controlled by, the controller 124 and/or the processor 126. The patterned light 120 is variable or configurable with respect to one or more of a light intensity, a hue of the patterned light output by the illumination source 118, a saturation of the patterned light 120, and one or more colors output by the illumination source 118.

The first section 130 of the first composite ply 104 is illuminated by the patterned light 120 from the illumination source 118, while a second section 132 of the first composite ply 104 is not illuminated by the patterned light 120, but is illuminated by another illumination source (not individually depicted for simplicity) such as ambient lighting or a dedicated light source. As depicted, the feedback camera 116 is configured to image the first section 130 of the first composite ply 104 (i.e., the patterned light that is reflected from the first section 130). The background camera 114 is configured to image the second section 132 of the first composite ply 104 (i.e., the light that is reflected from the second section 132), for example, under illumination by white light. One or more of the background camera 114 and the feedback camera 116 can include a charge coupled device (CCD) imager, a complementary metal oxide semiconductor (CMOS) imager, or another suitable imager. One or more of the background camera 114 and the feedback camera 116 can be a high-speed video camera.

The display 122 coupled to the controller 124 displays the output of the feedback camera 116 for review by an operator as described below.

As discussed above, the surface color of composite or metallic structures can camouflage or mask foreign materials on the surface of the composite. Conventional inspection systems are generally ineffective at reliably detecting these foreign materials, particularly when the foreign material is of the same or similar composition, color, and texture as the composite layer. Composite plies can have a high carbon content that provides a dark background and defects can include dark carbon fibers that are difficult to image on the dark carbon background.

In an implementation of the present teachings, the processor 126 of the inspection system 100 depicted in FIG. 1 performs image processing and comparison of a first output (e.g., a first data set) derived from the feedback camera 116 with a second output (a second data set) derived from the background camera 114. The processor 126, through the controller 124, can then modify the patterned light 120 output by the illumination source 118. Once the patterned light 120 has been modified according to a pattern determined by the processor 126 based on the image processing and comparison, the first output from the feedback camera 116 can then be compared again to the second output from the background camera 114, which is used to modify the patterned light 120 output by the illumination source 118. This series of comparisons and resulting changes in the patterned light output by the illumination source can continue in an attempt to match or camouflage the background (i.e., to cancel out background colors; to homogenize light reflected from the background of the first section of the first composite ply) such that only the foreign material(s), crack(s), pit(s), and/or other surface anomalies or defects are differentiated from the background within the image taken by the feedback camera 116. The qualities and characteristics of the patterned light 120 can be adjusted by the controller 124, for example, until background features of the first composite ply 104 imaged by the feedback camera 116 become sufficiently washed out that any defects are imaged with a high contrast compared to the background. Further, a first image of the surface of the first composite ply 104 can be taken prior to illumination with the patterned light 120 and compared to and evaluated with a second image of the surface of the first composite ply 104 taken subsequent to the illumination with the patterned light 120 to determine the effectiveness of the patterned light 120, which may be further adjusted to further contrast any surface defect(s) with the background surface. Once the processor 126 determines this final state has been reached or approximated through the process of feedback control of the illumination source 118, the controller 124 can display the image on the display 122 for viewing by an operator, who can then correct the surface anomaly. The correction may include removing the foreign material, repositioning the first composite ply 104, repairing a surface defect or other defect in the first composite ply 104, or another correction.

This technique is enabled, at least in part, by feedback control in individually selecting from over one million colors, variable hue, variable saturation, and variable patterns that can be output by the illumination source 118 onto the first section 130 of the first composite ply 104. A suitable patterned light 120 that subtracts the background is further enabled, at least in part, by the second output derived by the background camera when the background is illuminated by light such as white light. The background imaged by the background camera 114 can be analyzed by the processor 126, which then alters the patterned light 120 to homogenize the reflectance of the background, and/or to camouflage the background, in the first section 130. By homogenizing the reflectance and/or camouflaging the background of the first section 130, contrast of anomalies and/or defects such as foreign materials, cracks, pits, etc., is increased, thereby improving the detection of these anomalies and/or defects. The illumination source 118 can simultaneously produce several million shades of color per second while varying the hue, saturation, intensity, and pattern, which can be selected by the processor 126, thereby adapting the viewing environment to enhance the ability to detect defects. The adjustment of the patterned light 120 with respect to one or more of color, intensity, hue, and saturation aids in distinguishing an inherent pattern of the background from anomalies that, under white light, may be camouflaged.

Figure 3:
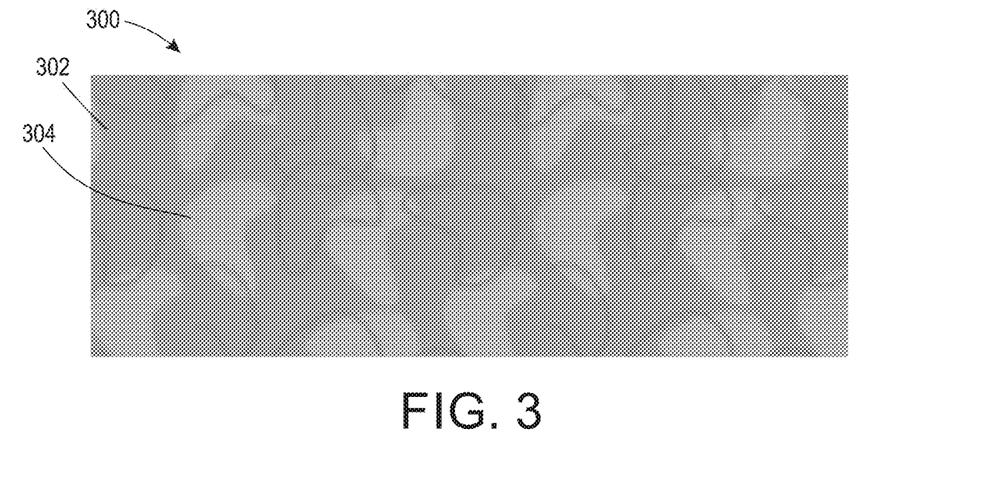
FIG. 3 depicts a representation of a background and a defect of a workpiece under white light or other lighting.
Figure 4:
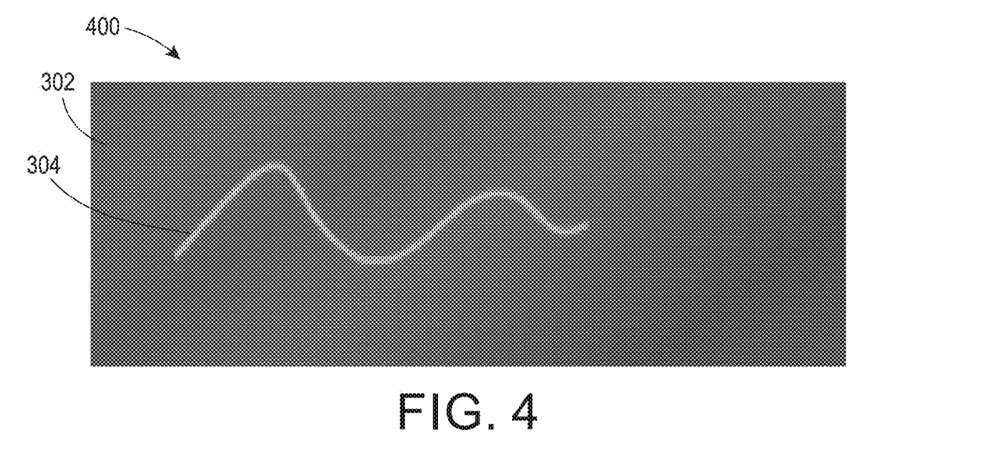
FIG. 4 depicts the FIG. 3 structure when illuminated with a patterned light according to the present teachings.

FIG. 3 represents a first view 300 of a background 302 of a portion of a workpiece such as first composite ply 104 that might be imaged by a camera under white light illumination. The workpiece includes a defect 304 that is camouflaged by the background 302 and is difficult to detect, either visually or through conventional image processing. FIG. 4 represents a second view 400 of the same background 302 that might be imaged by feedback camera 116 under patterned light 120 after performing the feedback control of the illumination source 118 as described above. In FIG. 4, the light reflected from the background 302 is homogenized and the contrast of the defect 304 relative to the background 302 is increased, and is more easily detected under the patterned light 120 after performing the feedback control than under the white light or ambient light illumination of FIG. 3.

In contrast to techniques such as "camouflage breaking," the present disclosure does not involve or rely on polarization to enhance defect detection. Instead, the present teachings may include homogenizing the background reflectance such that the reflectance from the background becomes uniform with respect to pattern and reflected light intensity, thereby camouflaging the background and enhancing contrast and detection of defects. The inspection system 100 uses the background imaged by the background camera 114 at the second section 132 to estimate the background at the first section 130, and to alter the patterned light 120 to further improve camouflaging of the background at the first section 130. The light effect or light pattern applied to patterned light 120 thereby camouflages the background at first section 130 by introducing a light mechanism that subtracts the background out of the displayed image. In other words, the patterned light 120 is adjusted, controlled, and/or varied such that the light reflected from the first section 130 of the first composite ply 104 is homogenous or uniform across the image with respect to one or more of pattern, hue, saturation, color, and intensity. In effect, a new homogenous or camouflage background is created that, when imaged using the feedback camera 116, shows surface anomalies. For example, while the background 302 of FIG. 3 under illumination of white light camouflages the defect 304, the background 302 of FIG. 4 under illumination of the patterned light 120 subsequent to feedback control highlights the defect 304 and eases detection of the defect 304.

Figure 5:
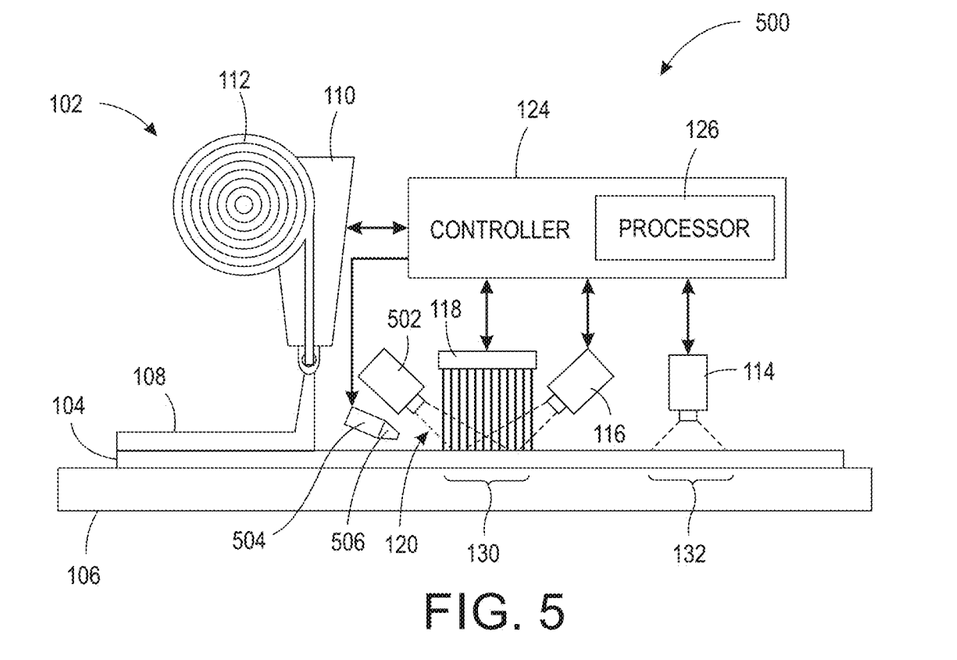
FIG. 5 is a schematic depiction of another inspection system according to an implementation of the present teachings.

As discussed above, the inspection system 100 of FIG. 1 includes a display 122 that displays output from the feedback camera 116 that is viewable by an operator. If a surface anomaly is detected, an operator can correct the anomaly using one of the methods described above, or a different method. FIG. 5 depicts another inspection system 500 that includes automated correction of a surface anomaly. It will be noted that features or inspection system substructures that are similar to those depicted and described with reference to FIG. 1 are similarly numbered and not described in detail for the FIG. 5 depiction for simplicity.

The inspection system 500 includes an inspection camera 502 electrically coupled to the controller 124 and the processor 126. The inspection camera 502 images the first section 130 of the first composite ply 104 and outputs a third output (e.g., a third data set) to the processor 126. The processor 126 analyzes data from the feedback camera 116 and the background camera 114 to detect defects. Upon detection of a defect 304 (FIG. 4) on or within the workpiece 104, the processor 126 uses the inspection camera 502 to control movement of a pressure conveying system 504 to position the pressure conveying system 504, for example, a nozzle 506 of the pressure conveying system, relative to the defect. The pressure conveying system can be or include a blower that outputs a stream of air toward the defect, a vacuum to apply a vacuum force to the defect, or both a blower and a vacuum that may be individually and selectively activated or engaged. Once the nozzle 506 is properly positioned relative to the defect by the processor 126 using the controller 124 and the inspection camera 502, the controller 124 activates or engages the pressure conveying system in an attempt to dislodge the defect from the workpiece 104.

Figure 6:
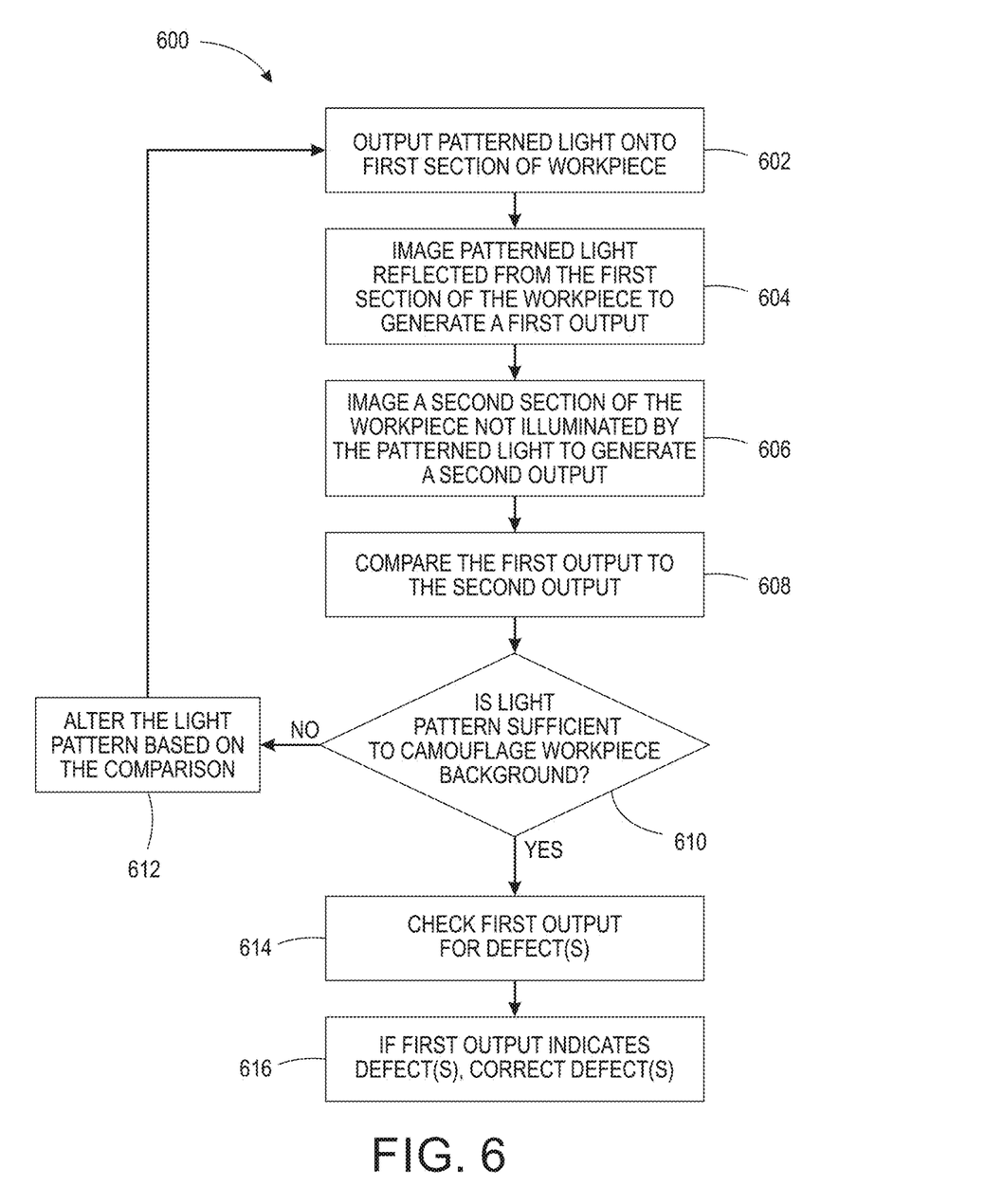
FIG. 6 is a flow chart or flow diagram of a method for inspecting a workpiece according to an implementation of the present teachings.

A method 600 for inspecting a workpiece is shown in the flow chart or flow diagram of FIG. 6. The method 600 may proceed by operation or use of one or more of the structures depicted in the figures as described above, and thus is described with reference to FIGS. 1-5; however, it will be appreciated that the method 600 is not limited to any particular structure or use unless expressly stated herein. It will be further appreciated that while the method 600 is described as a series of acts or events, the present teachings are not limited by the ordering of such acts or events. Some acts may occur in different orders and/or concurrently with other acts or events apart from those described herein. Further, a method in accordance with the present teachings may include other acts or events that have not been depicted for simplicity, while other depicted acts or events may be removed or modified.

The method for inspecting a workpiece can begin by outputting a patterned light 120 onto a first section 130 of a workpiece 104 as at 602. The patterned light 120 may be output using an illumination source 118 such as an OLED array 200, or another illumination source 118. The patterned light 120 reflected from the first section 130 of the workpiece 104 is then is then imaged to generate a first output as at 604, for example, using a feedback camera 116 to produce the first output. As shown at 606, a second section 132 of the workpiece 104 that is not illuminated by the patterned light 120 is imaged to generate a second output, for example, using a background camera 114 to produce the second output. The first output is compared to the second output as at 608 using, for example, pattern analysis. If it is determined at 610 that the patterned light is not sufficient to camouflage the workpiece background as at 612, the patterned light 120 is altered, for example, using the processor 126 and the controller 124, and the altered patterned light 120 is output onto the first section 130 of the workpiece 104 as at 602, where the process (e.g., feedback control process) continues according to the flow diagram of FIG. 6. If it is determined at 610 that the patterned light 120 is sufficient to camouflage the workpiece background, the first output is checked or analyzed to determine whether defects exist in the first section 130 as at 614. For example, the first output may be displayed on a display 122 for review by an operator according to FIG. 1, or the processor 126 may perform an analysis of available data according to FIG. 5. If the first output indicates that defects are present as at 616, the defects are corrected, for example, by an operator or using the inspection camera 502 and the pressure conveying system 504.

Figure 7:
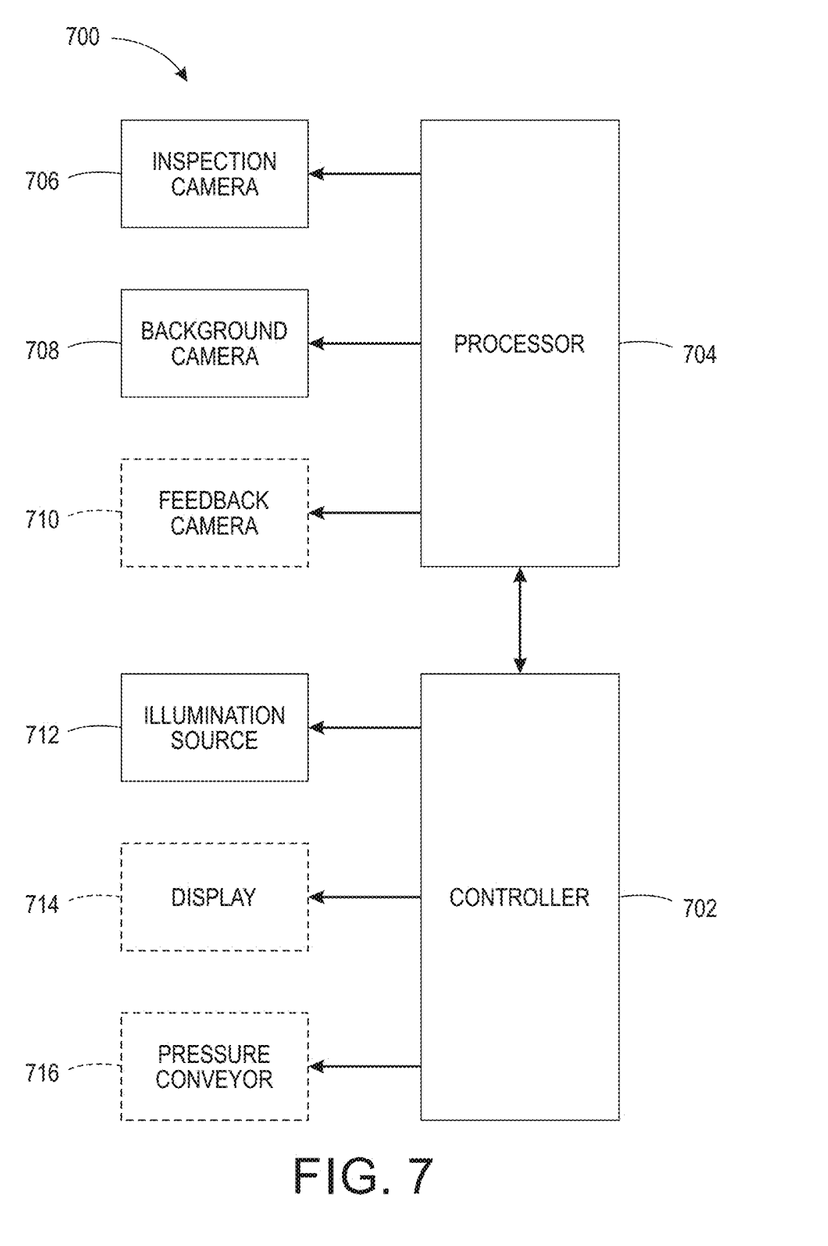
FIG. 7 is a functional block diagram according to an implementation of the present teachings.

It is contemplated that each of the components or subsystems of the inspection system may be electrically and communicatively interconnected in various configurations, depending on the design of the inspection system. FIG. 7 is an exemplary functional block diagram depicting an inspection system 700 according to an implementation of the present teachings. Elements that are optional for some implementations are depicted in phantom, although other items not depicted in phantom may also be optional for some other implementations. Further, an inspection system 700 may include other structures that, for simplicity, have not been depicted or described.

The inspection system 700 includes a controller 702 and a processor 704 that may be part of, or separate from, the controller 702. An inspection camera 706, a background camera 708, and a feedback camera 710 each supply image data to the processor 704 for analysis, which is used to control an illumination source 712, a display 714, and a pressure conveyor 716 as depicted. The inspection system 700 can be employed to perform the inspection of a workpiece as described above, or for other uses.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or implementations of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. As used herein, the term "one or more of" with respect to a listing of items such as, for example, A and B, means A alone, B alone, or A and B. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated implementation. Finally, "exemplary" indicates the description is used as an example, rather than implying that it is an ideal. Other implementations of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

The invention claimed is:

1. A method for inspecting a workpiece, comprising:
outputting a patterned light onto a first section of the workpiece using an illumination source, wherein:
the illumination source comprises a plurality of illumination elements;
the plurality of illumination elements of the illumination source comprises at least one million organic light emitting diodes (OLEDs);
each illumination element of the plurality of illumination elements is individually controllable with respect to light intensity; and
the first section of the workpiece reflects the patterned light;
imaging the patterned light reflected from the first section of the workpiece using a feedback camera to generate a first output;
imaging a second section of the workpiece that is not illuminated by the illumination source using a background camera to generate a second output;
comparing the first output to the second output; and
altering a light pattern of the patterned light output by the illumination source, wherein the altering of the patterned light comprises individually controlling a light intensity of each of the OLEDs, thereby changing one or more of an intensity, a hue, a saturation, and a color of the patterned light based on the comparing of the first output to the second output and increasing a contrast of one or more defects located in the first section of the workpiece.

2. The method of claim 1, wherein each OLED is configured to output at least 1000 lux.

3. The method of claim 1, further comprising displaying data obtained from the first output from the feedback camera onto a display for inspection by an operator.

4. The method of claim 1, further comprising:
imaging the patterned light reflected from the first section of the workpiece using an inspection camera to generate a third output;
sending data obtained from the third output from the inspection camera to a processor; and
using the processor to analyze the data obtained from the third output to detect the one or more defects in the first section of the workpiece.

5. The method of claim 4, further comprising:
detecting the one or more defects on or within the workpiece during the comparing;
using a controller to position a pressure conveying system relative to the one or more defects; and
activating the pressure conveying system to dislodge the one or more defects from the workpiece.

6. The method of claim 5, wherein the activating of the pressure conveying system comprises at least one of activating a blower to output a stream of air to dislodge the one or more defects and activating a vacuum to apply a vacuum force to the one or more defects.

7. The method of claim 1, wherein the altering of the patterned light results in homogenizing the light reflected from the second section of the workpiece, except for light reflected from the one or more defects.

8. The method of claim 1, further comprising:
depositing a first composite layer of the workpiece onto a working surface using a composite layup system, wherein the first section of the workpiece is a first section of an aircraft subassembly and the second section of the workpiece is a second section of the workpiece;
performing the imaging of the patterned light reflected from the first section of the aircraft subassembly;
depositing a second composite layer of the aircraft subassembly onto the first composite layer;
outputting the patterned light onto a first section of the second composite layer using the illumination source, wherein the first section of the second composite layer reflects the patterned light; and
imaging the patterned light reflected from the first section of the second composite layer using the feedback camera to generate a third output.

9. An inspection system, comprising:
an illumination source configured to output a patterned light and to illuminate a first section of a workpiece with the patterned light, wherein:
the illumination source comprises a plurality illumination elements and each illumination element of the plurality of illumination elements is individually controllable with respect to light intensity;
the illumination source is an organic light emitting diode (OLED) display; and
the plurality of illumination elements comprises a plurality of OLEDs;
a feedback camera configured to image the patterned light from the illumination source that is reflected from the first section of the workpiece, and to generate a first output;
a background camera configured to image a second section of the workpiece that is not illuminated by the illumination source, and to generate a second output; and
a controller coupled to the illumination source, the feedback camera, and the background camera, wherein the controller is configured to alter a light pattern of the patterned light output by the illumination source by individually controlling each OLED of the plurality of OLEDs with respect to the light intensity, thereby changing one or more of an intensity, a hue, a saturation, and a color of the patterned light based on a comparison of the first output to the second output, thereby increasing a contrast of one or more defects located in the first section of the workpiece.

10. The inspection system of claim 9, wherein the plurality of illumination elements comprises at least one million OLEDs.

11. The inspection system of claim 9, wherein each OLED is configured to output an intensity of at least 1000 lux and to have a luminous efficiency of at least 100 lumens per Watt.

12. The inspection system of claim 9, further comprising a visual display for displaying data obtained from the first output generated by the feedback camera.

13. The inspection system of claim 12, wherein the visual display is configured to display an image of the one or more defects located in the first section of the workpiece imaged by the feedback camera for review by an operator.

14. The inspection system of claim 9, further comprising an inspection camera for imaging the second section of the workpiece during the illumination by the illumination source and to provide a third output to the controller.

15. The inspection system of claim 14, further comprising a pressure conveying system electrically coupled to, and controlled by, the controller, wherein the controller is configured to position the pressure conveying system relative to the one or more defects detected during the comparison using the third output from inspection camera, and to activate the pressure conveying system to dislodge the one or more defects from a surface of the workpiece.

16. The inspection system of claim 15, wherein the pressure conveying system comprises at least one of a blower configured to output a stream of air to dislodge the one or more defects and a vacuum configured to apply a vacuum force to the one or more defects.

17. The inspection system of claim 9, wherein the illumination source comprises an array of at least one million of the illumination elements, and the controller is configured to vary the intensity, hue, saturation, color, and the light pattern of the patterned light output by the illumination source such that the feedback camera images an illuminated surface of the workpiece that is homogenous with respect to intensity, hue, saturation, and color, except for the one or more defects on or within the surface of the workpiece.

18. An aircraft manufacturing line, comprising:
a composite layup system configured to deposit a plurality of layers of a composite aircraft subassembly onto a working surface; and
an inspection system for inspecting the composite aircraft subassembly during a deposition of the plurality of layers, the inspection system comprising:
an illumination source configured to output a patterned light and to illuminate a first section of a workpiece with the patterned light, wherein:
the illumination source comprises a plurality of illumination elements and each illumination element of the plurality of illumination elements is individually controllable with respect to light intensity;
the illumination source is an organic light emitting diode (OLED) display; and
the plurality of illumination elements comprises a plurality of OLEDs;

a feedback camera configured to image the patterned light from the illumination source that is reflected from the first section of the workpiece, and to generate a first output;

a background camera configured to image a second section of the workpiece that is not illuminated by the illumination source, and to generate a second output; and a controller coupled to the illumination source, the feedback camera, and the background camera, wherein the controller is configured to alter a light pattern of the patterned light output by the illumination source by individually controlling each OLED of the plurality of OLEDs with respect to the light intensity, thereby changing one or more of an intensity, a hue, a saturation, and a color of the patterned light based on a comparison of the first output to the second output, thereby increasing a contrast of one or more defects located in the first section of the workpiece.

19. The aircraft manufacturing line of claim 18, wherein the plurality of illumination elements comprises at least one million OLEDs.

20. The aircraft manufacturing line of claim 18, wherein each OLED is configured to output an intensity of at least 1000 lux and to have a luminous efficiency of at least 100 lumens per Watt.

* * * * *